United States Patent [19]

Imaki et al.

[11] Patent Number: 5,023,268

[45] Date of Patent: Jun. 11, 1991

[54] 3-PHENOXY (OR PHENYLTHIO)-CYCLOPENTANECARBONYLAMINO ACID ANALOGUES

[75] Inventors: Katsuhiro Imaki, Tsuzuki; Tadao Okegawa, Yawata; Yoshinobu Arai, Mishima, all of Japan

[73] Assignee: Ono Pharmaceutical Co., Ltd., Osaka, Japan

[21] Appl. No.: 404,713

[22] Filed: Sep. 8, 1989

Related U.S. Application Data

[62] Division of Ser. No. 268,623, Nov. 7, 1988, Pat. No. 4,888,351, which is a division of Ser. No. 158,457, Feb. 22, 1988, Pat. No. 4,829,078, which is a division of Ser. No. 942,109, Dec. 16, 1986, Pat. No. 4,783,476.

[30] Foreign Application Priority Data

Dec. 16, 1985 [JP] Japan .................. 60-281203

[51] Int. Cl.$^5$ ................ A61K 31/415; A61K 31/405; A61K 31/195; C07D 233/64; C07D 229/18; C07D 207/12

[52] U.S. Cl. ..................................... 514/400; 514/419; 514/423; 514/561; 514/562; 514/563; 548/344; 548/496; 548/535; 562/427; 562/431; 562/435; 562/444; 562/445; 562/448

[58] Field of Search ............... 562/427, 431, 435, 444, 562/445, 448; 548/344, 496, 535; 514/397, 400, 419, 423, 561, 562, 563

[56] References Cited

U.S. PATENT DOCUMENTS

| | | | |
|---|---|---|---|
| 3,984,465 | 10/1976 | Cragoe et al. | 514/869 |
| 4,012,524 | 3/1977 | Cragoe et al. | 549/79 X |
| 4,070,539 | 1/1978 | Cragoe et al. | 514/869 |
| 4,096,267 | 6/1978 | Cragoe et al. | 549/77 X |
| 4,166,061 | 8/1979 | Mastrocola | 549/72 |
| 4,640,931 | 2/1987 | Imaki et al. | 514/510 |

Primary Examiner—José G. Dees
Assistant Examiner—Vera C. Clarke
Attorney, Agent, or Firm—Sughrue, Mion, Zinn, Macpeak & Seas

[57] ABSTRACT

Compounds related to 3-phenoxy (or phenylthio) cyclopentanecarbonylamino acid, processes for their preparation, and treating agents for cerebral edema containing the compounds as active ingredients are described. The compounds are represented by the following formula:

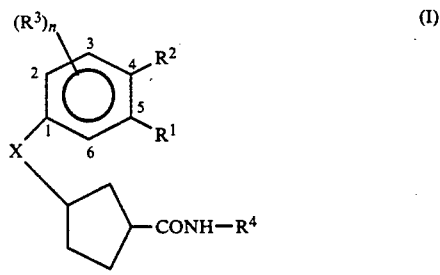

The compounds of the present invention and their non-toxic salts have a potent inhibitory effect on the development of cerebral edema.

6 Claims, No Drawings

3-PHENOXY (OR PHENYLTHIO)-CYCLOPENTANECARBONYLAMINO ACID ANALOGUES

This is a division of application Ser. No. 07/268,623, filed Nov. 7, 1988, now U.S. Pat. No. 4,888,351, which is a divisional of application Ser. No. 07/158,457 filed Feb. 22, 1988, now U.S. Pat. No. 4,829,078, which is a divisional of Ser. No. 06/942,109, filed Dec. 16, 1986, now U.S. Pat. No. 4,783,476.

1. Field of the invention

This invention relates to novel derivatives of 3-phenoxy (or phenylthio)cyclopentanecarbonylamino acid, processes for their preparation and treating agents for cerebral edema containing them as active ingredients.

2. Prior arts

Heretofore, derivatives of 5-substituted-indan-1-one for the purpose of treatment of cerebral edema have been known. For example, in the specification of the European Patent Publication No. 47011, it was proposed that the compounds of the general formula:

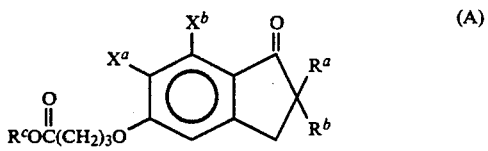

(wherein $X^a$ and $X^b$ represent a halogen atom, $R^a$ represents a lower alkyl group of 1 to 6 carbon atoms, $R^b$ represents a hydrogen atom, a lower alkyl group of 1 to 4 carbon atoms, a cycloalkyl group of 3 to 6 carbon atoms, a lower cycloalkyl-lower alkyl group of 4 to 7 carbon atoms, or a phenyl and $R^c$ represents a hydrogen atom, a lower alkyl group of 1 to 6 carbon atoms or a carboxy-lower alkyl group of 2 to 6 carbon atoms) and their salts may be used for treatment of cerebral edema.

In the general formula (A), the compound wherein $X^a$ and $X^b$ represent chlorine atoms, $R^a$ represents a methyl group, $R^b$ represents a cyclopentyl group and $R^c$ represents a hydrogen atom, i.e. (+)-4-[((2R)-2-cyclopentyl-2-methyl-6,7-dichloro-1-oxoindan-5-yl)oxy]butyric acid of the formula:

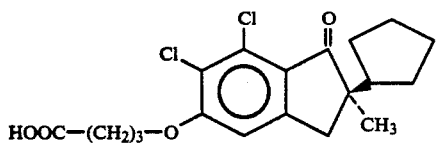

has been known as "DCPIB", and whose inhibitory effect on cerebral edema was described in detail in Journal of Medicinal Chemistry, Vol. 25 (No. 5), 567 (1982).

And further, compounds wherein cyclopentanone in their indane skeleton is opened were described in the specification of the British Patent No. 1548729 and the U.S. Pat. No. 3,758,506. For example, in the specification of the British Patent No. 1548729, the compounds of the general formula:

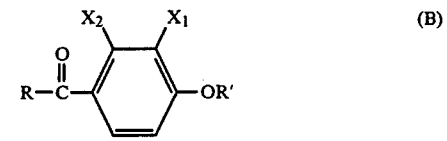

(wherein R represents a phenyl ring, a substituted phenyl ring or a naphthyl group, R' represents a formula: —$CH_2COOH$ or a methyltetrazol group, and $X_1$ and $X_2$ represent a halogen atom or a lower alkyl group respectively, or a naphthalene ring when both of them and the phenyl ring substituted by them join with one another) were proposed. As the main activity of the above compounds is diuresis and reducing blood pressure, therefore these compounds are much different from DCPIB.

PURPOSE

The purpose of the present invention is the proposal of the novel compounds which have inhibitory effect on cerebral edema.

MEANS TO ACCOMPLISH THE PURPOSE

As a result of energestic investigations on purpose to find the novel compound having an inhibitory effect on cerebral edema, the present inventors have before found the desired compounds, and many patent applications thereon have been filed.

For example, in the specification of the European Patent Publication No. 181100 (published on May 14th, 1986), the derivatives of 3-(indane-5-yloxy (or thio))cyclopentanecarboxylic acid of the general formula:

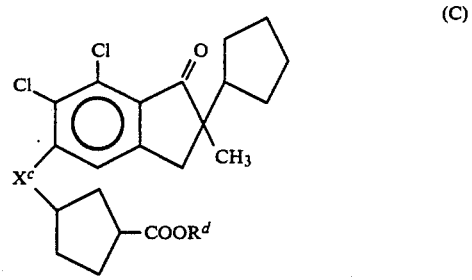

(wherein $X^c$ represents an oxygen atom or a sulfur atom, $R^d$ represents a hydrogen atom or an alkyl group of 1 to 4 carbon atoms) were porposed, and further in the specification of the Japanese Patent Application No. 60-157990 (filed on July 19th, 1985) and the U.S. patent application Ser. No. 06/887772 (filed on July 21st, 1986), the derivatives of 3-[(4-aroyl)phenoxy (or phenylthio)]cyclopentanecarboxylic acid of the general formula:

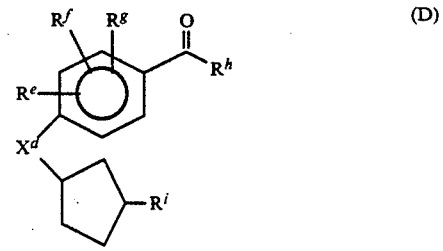

[wherein $X^d$ represents an oxygen atom or a sulfur atom, $R^e$, $R^f$ and $R^g$ represent a hydrogen atom, a halogen atom, an alkyl group of 1 to 4 carbon atoms, independently, or

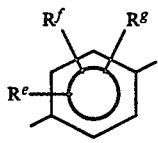

in the general formula (D) represents

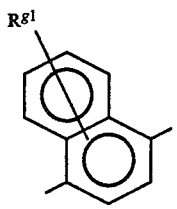

(wherein $R^{g'}$ represents a hydrogen atom, a halogen atom or an alkyl group of 1 to 4 carbon atoms), $R^h$ represents the group of the general formula:

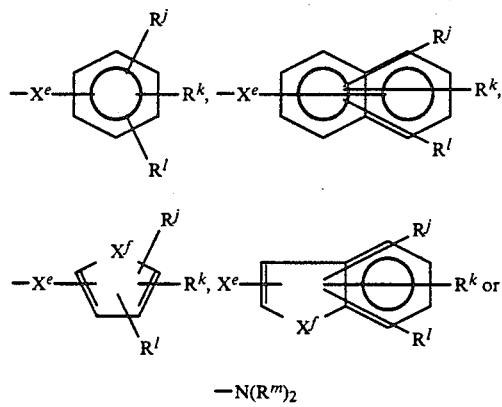

$-N(R^m)_2$ (wherein $X^f$ represents an oxygen atom or a sulfur atom, $R^j$, $R^k$ and $R^l$ represent a hydrogen atom, a halogen atom, a nitro group, an alkyl group of 1 to 4 carbon atoms, a hydroxy group or an alkoxy group of 1 to 4 carbon atoms, independently, two of $R^m$ represent a hydrogen atom, an alkyl group of 1 to 4 carbon atoms or a phenyl group, independently, and $X^e$ represents a single-bond or an alkylene group or an alkenylene group of 1 to 4 carbon atoms), $R^i$ represents 2-tetrazolyl group or the group of the general formula: $-COOR^n$ (wherein $R^n$ represents a hydrogen atom or an alkyl group of 1 to 4 carbon atoms)] were proposed.

The compounds of the general formulae (C) and (D) have a powerful inhibitory effect on cerebral edema.

Now, the present inventors have synthesized novel compounds wherein various amino acids are bonded to the COOR group of the compounds of the general formula (C) or to $R^5$ group of the compounds of the general formula (D), and have found that these compounds have a strong inhibitory activity on cerebral edema, having completed the present invention.

COMPARISON WITH PRIOR ARTS

The compounds of the present invention are much different from the compounds of the general formulae (A) and (B) described in the above item [Prior Art] in chemical structure.

That is, the compounds of the present invention have the chemical structure that cyclopentylene group

is introduced in place of a trimethylene group [$-(CH_2)_3-$] between an indanyloxy group and a carboxy group in a side chain of compound of the general formula (A), or in place of a methylene group ($-CH_2-$) in $-CH_2COOH$ group represented by R' group in compounds of the general formula (B), and further that various amino acids are bonded to the carboxy group ($-COOH$) linked to the said trimethylene or methylene group. These chemical modifications have never been carried out in this technical field, and, therefore, the compounds of the present invention are considered to have quite novel chemical structure which is not anticipated from those of compounds of the general formulae (A) and (B).

CONSTITUTION OF THE INVENTION

Accordingly, the present invention relates to derivatives of 3-phenoxy (or phenylthio)cyclopentanecarbonylamino acid of the general formula:

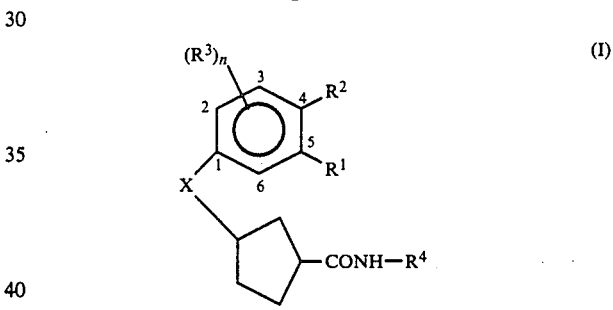

[wherein $R^1$ and $R^2$ are:

(i) $R^1$, $R^2$ and carbon atoms to which $R^1$ and $R^2$ are linked, together represent the group of the general formula:

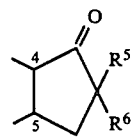

(wherein $R^5$ and $R^6$ represent a hydrogen atom, an alkyl group of 1 to 6 carbon atoms, a cycloalkyl group of 3 to 6 carbon atoms, a cycloalkyl-alkyl group of 4 to 7 carbon atoms or a phenyl group, independently, with the proviso that $R^5$ and $R^6$ do not represent hydrogen atoms at the same time), or (ii) $R^1$ represents a hydrogen atom and $R^2$ represents the group of the general formula: $-COR^7$ (wherein $R^7$ represents the group of the general formula:

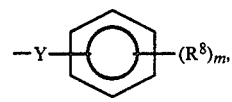

-continued

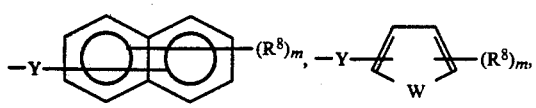

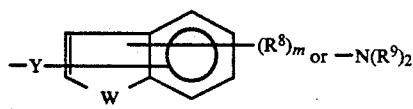

(wherein Y represents a single-bond, an alkylene group or an alkenylene group of 1 to 4 carbon atoms, W represents an oxygen atom or a sulfur atom, m represents an integer of 1 to 3, $R^8$ represents a hydrogen atom, a halogen atom, a nitro group, a hydroxy group or an alkyl group or an alkoxy group of 1 to 4 carbon atoms, with the proviso that when m represents an integer of two or more, plural $R^8$s may be different each, and $R^9$ represents a hydrogen atom, an alkyl group of 1 to 4 carbon atoms or a phenyl group, with the proviso that two of $R^9$ may be different each)), $R^3$ represents a hydrogen atom, a halogen atom, an alkyl group of 1 to 4 carbon atoms or two of $R^3$ and a phenyl group to which two of $R^3$ are linked, together represent a naphthyl group of the general formula:

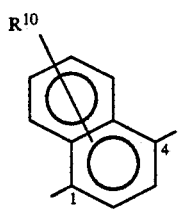

(wherein $R^{10}$ represents a hydrogen atom, a halogen atom or an alkyl group of 1 to 4 carbon atoms), with the proviso that when $R^1$ represents a hydrogen atom, the hydrogen atom may be replaced by $R^3$, and n represents an integer of 1 to 3, with the proviso that when n represents an integer of two or more, plural $R^3$s may be different each, X represents an oxygen atom or a sulfur atom and $R^4$ represents an amino acid-residue], and non-toxic salts thereof, and methods for their preparation and treating agents for cerebral edema containing them as active ingredients.

It is to be understood that alkyl, alkylene, alkenylene and alkoxy groups within the definitions of various symbols in this specification and the accompanying claims may be straight or branched-chain.

In the structural formulae in this specification, the broken line (---) indicates the α-configuration, the bold line (▬) indicates the β-configuration, the wavy line (〜) indicates the α-configuration or the β-configuration or a mixture thereof. As will be apparent to those skilled in the art, the compounds of the general formula (I) have several asymmetric centers, for example, the first and the third carbon atoms of a cyclopentylene group in the side chain and the carbon atom in several kind of amino acid-residue. Furthermore, when $R^1$ and $R^2$ together represent a cyclopentenone group, the carbon atom to which $R^5$ and $R^6$ are bonded is the asymmetric center, and further when $R^1$, $R^2$ or $R^3$ represents a branched-alkyl group, there is possibility of occurring the other asymmetric center. As is well known, the presence of asymmetric center leads to the isomers. However, all of each isomer and the mixture thereof are contained in the general formula (I).

In the general formula (I), as an alkyl group of 1 to 6 carbon atoms represented by $R^5$ and $R^6$, in the group represented by $R^1$ and $R^2$, a methyl group, an ethyl group, a propyl group, a butyl group, a pentyl group, a hexyl group and isomers thereof are cited, and as a cycloalkyl group of 3 to 6 carbon atoms, a cyclopropyl group, a cyclobutyl group, a cyclopentyl group and a cyclohexyl group are cited, and further as a cycloalkyl-alkyl group of 4 to 7 carbon atoms, a cyclopropyl-methyl group, cyclopropylethyl group, a cyclopropyl-propyl group, a cyclopropylbutyl group, a cyclobutyl-methyl group, a cyclobutylethyl group, a cyclobutyl-propyl group, a cyclopentylmethyl group, a cyclopentylethyl group, a cyclohexylmethyl group and isomers thereof are cited. Preferably, one of $R^5$ and $R^6$ represents an alkyl group of 1 to 6 carbon atoms, and the other group represents a cyclopentyl group, and most preferably, one of $R^5$ and $R^6$ represents a methyl group, the other group represents a cyclopentyl group.

As an alkylene group of 1 to 4 carbon atoms represented by Y in $R^7$, a methylene group, an ethylene group, a trimethylene group, a tetramethylene group and isomers thereof are cited, and as an alkenylene group of 1 to 4 carbon atoms, a vinylene group, a propenylene group, a butenylene group and isomers thereof are cited. Preferably Y represents a single-bond, a methylene group and a vinylene group.

As a halogen atom represented by $R^8$, a fluorine atom, a chlorine atom, a bromine atom and iodine atom are cited, and as an alkyl group of 1 to 4 carbon atoms, a methyl group, an ethyl group, a propyl group, a butyl group and isomers thereof are cited, and as an alkoxy group of 1 to 4 carbon atoms, a methoxy group, an ethoxy group, a propoxy group, a butoxy group and isomers thereof are cited.

As an alkyl group of 1 to 4 carbon atoms represented by $R^9$, a methyl group, an ethyl group, a propyl group, a butyl group and isomers thereof are cited.

As preferred $R^7$, the following groups are cited:

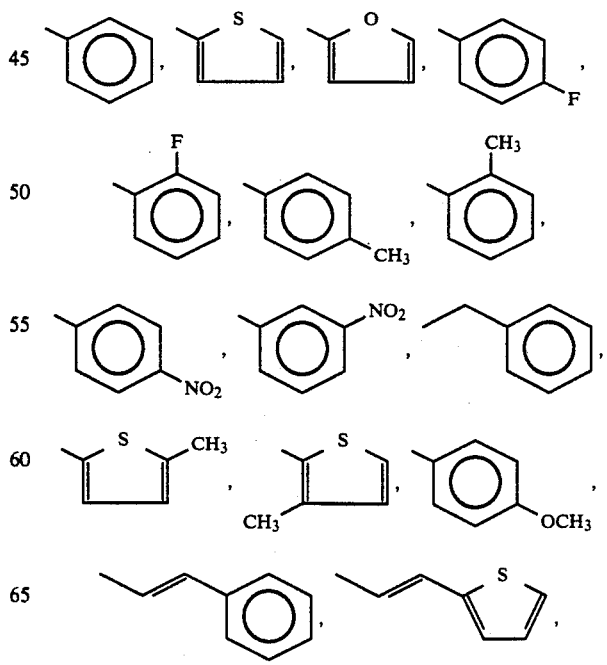

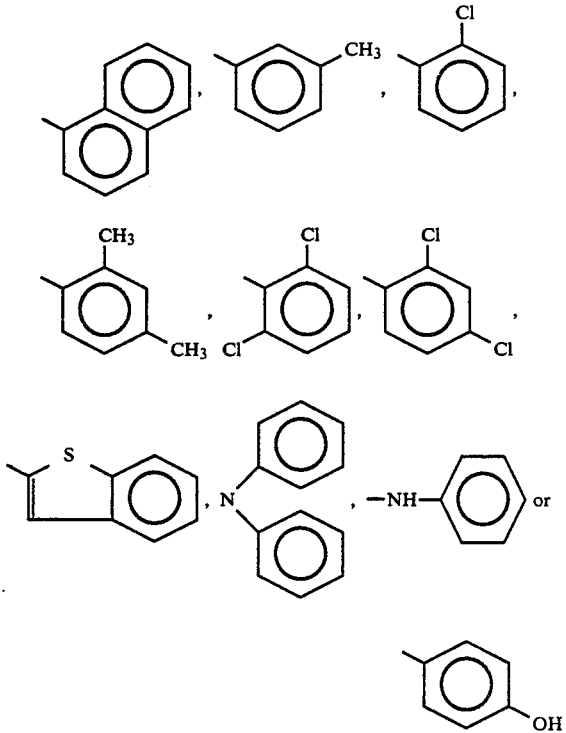

As a halogen atom represented by $R^3$, a fluorine atom, a chlorine atom, a bromine atom and an iodine atom are cited, and as an alkyl group of 1 to 4 carbon atoms, a methyl group, an ethyl group, a propyl group, a butyl group and isomers thereof are cited.

As a halogen atom and an alkyl group of 1 to 4 carbon atoms represented by $R^{10}$ in $R^3$, the same atom and group represented by $R^3$ are cited.

As preferred $(R^3)n$, all of $R^3$ represents a hydrogen atom, or $R^3$ represents a fluorine atom, a chlorine atom, a methyl group or a nitro group and n represents an integer of 1 to 2.

By the term "amino acid-residue", represented by $R^4$, is meant the chemical structure in which an amino group ($-NH_2$ group) is eliminated from various amino acids. For example, as neutral amino acid alanine, β-alanine, asparagine, 4-aminobutyric acid (GABA), glycine, glutamine, serine, phenylalanine, cysteine, 4-amino-3-hydroxybutyric acid (GABOB), tryptophane, leucine, isoleucine, threonine, methionine, proline and valine are cited, and as acidic amino acid, glutamic acid and asparaginic acid are cited, and further as basic amino acid, lysine, arginine and histidine are cited. Basic amino acids have two amino groups, and the carboxyl group attached to the end of cyclopentylene group may be combined with either amino group. As preferred amino acid, neutral amino acid and acidic amino acid are cited, most preferred amino acid is acidic amino acid.

The symbol $R^4$ represents an amino acid residue having a carboxyl group. Therefore, the compounds of the general formula (I) may be converted into non-toxic salts thereof.

As for the stereo-configuration of the carbon atoms at the 1- and 3-positions of a cyclopentylene group, (1S,3S), (1R,3R), (1S,3R) and (1R,3S) are also preferable, and (1S,3S) and (1R,3R) which compose of a trans-configuration each other, are more preferable. Above all, (1S,3S) is the most preferable.

Preferred compounds of the general formula (I) of the present invention are, for example, as follows:

N-[(1S,3S)-3-[{(2RS)-2-methyl-6,7-dichloro-2-cyclopentyl-1-oxo-2,3-dihydro-1H-indene-5-yl}oxy]cyclopentanecarbonyl]glutamic acid, N-{(1S,3S)-3-(2,3-dichloro-4-benzoylphenoxy)cyclopentanecarbonyl}glycine, 4-{(1S,3S)-3-(2,3-dichloro-4-benzoylphenoxy)cyclopentanecarboxamido}butyric acid, N-{(1S,3S)-3-(2,3-dichloro-4-benzoylphenoxy)cyclopentanecarbonyl}alanine, N-{(1S,3S)-3-(2,3-dichloro-4-benzoylphenoxy)cyclopentanecarbonyl}-β-alanine, N-{(1S,3S)-3-(2,3-dichloro-4-benzoylphenoxy)cyclopentanecarbonyl}serine, N-{(1S,3S)-3-(2,3-dichloro-4-benzoylphenoxy)cyclopentanecarbonyl}asparaginic acid, N-{(1S,3S)-3-(2,3-dichloro-4-benzoylphenoxy)cyclopentanecarbonyl}asparagine, 4-{(1S,3S)-3-(2,3-dichloro-4-benzoylphenoxy)cyclopentanecarboxamido}-3-hydroxy butyric acid, N-{(1S,3S)-3-(2,3-dichloro-4-benzoylphenoxy)cyclopentanecarbonyl}glutamic acid, N-{(1S,3S)-3-(2,3-dichloro-4-benzoylphenoxy)cyclopentanecarbonyl}glutamine, N-[(1S,3S)-3-(2,3-dichloro-4-(2-fluorobenzoyl)phenoxy)cyclopentanecarbonyl]glutamic acid, N-{(1S,3S)-3-(4-benzoyl-1-naphthoxy)cyclopentanecarbonyl}glutamic acid, N-[(1S,3S)-3-{2,3-dichloro-4-(2-thenoyl)phenoxy}cyclopentane carbonyl]glutamic acid, N-[(1S,3S)-3-{2,3-dichloro-4-(1-naphthoyl)phenoxy} cyclopentane carbonyl]glutamic acid, N-{(1S,3S)-3-(2,3-dichloro-4-phenylacetylphenoxy)cyclopentane carbonyl}glutamic acid, N-{(1R,3R)-3-(2,3-dichloro-4-benzoylphenoxy)cyclopentanecarbonyl}glutamic acid, N-{(1R,3S)-3-(2,3-dichloro-4-benzoylphenoxy)cyclopentanecarbonyl}glutamic acid, and the corresponding compounds wherein the oxygen atom which is between the indanyl group or the phenyl group, and the cyclopentylene group, in the above compounds, is replaced by a sulfur atom.

NOMENCLATURE

The method for numbering the positions of carbon atoms in the compounds of the present invention is changed according to groups represented by $R^1$ and $R^2$ as follows.

(i) when $R^1$, $R^2$ and a phenyl group to which $R^1$ and $R^2$ are linked, together represent an indanyloxy group:

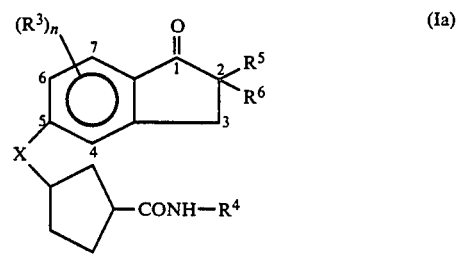

[wherein all groups are the same meaning as described hereinbefore], and (ii) when $R^1$ represents a hydrogen atom and $R^2$ represents a group of the general formula —$COR^7$:

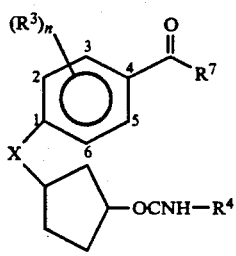

(Ib)

[wherein all groups are the same meaning as described hereinbefore].

In this specification including claims, the compounds are named as mentioned above.

PROCESSES FOR THE PREPARATION

The compounds of the present invention, of the general formula (I) may be prepared by the following scheme.

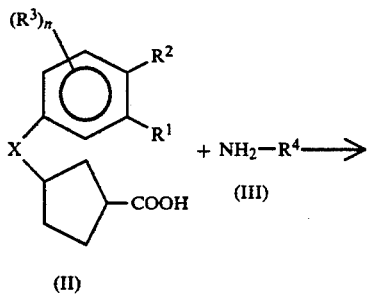

+ $NH_2$—$R^4$ ⟶

(II)

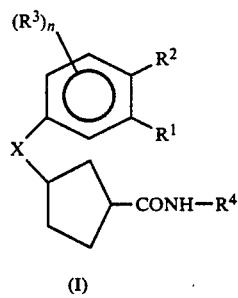

(I)

[wherein $R^1$ and $R^2$ are:

(i) $R^1$, $R^2$ and carbon atoms to which $R^1$ and $R^2$ are linked, together represent the group of the general formula:

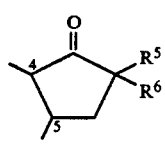

(wherein $R^5$ and $R^6$ represent a hydrogen atom, an alkyl group of 1 to 6 carbon atoms, a cycloalkyl group of 3 to 6 carbon atoms, a cycloalkyl-alkyl group of 4 to 7 carbon atoms or a phenyl group, independently, with the proviso that $R^5$ and $R^6$ do not represent hydrogen atoms at the same time), or (ii) $R^1$ represents a hydrogen atom and $R^2$ represents the group of the general formula: —$COR^7$ (wherein $R^7$ represents the group of the general formula:

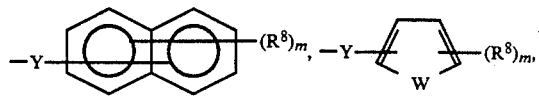

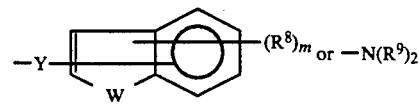

(wherein Y represents a single-bond, an alkylene group or an alkenylene group of 1 to 4 carbon atoms, W represents an oxygen atom or a sulfur atom, m represents an integer of 1 to 3, $R^8$ represents a hydrogen atom, a halogen atom, a nitro group, a hydroxy group or an alkyl group or an alkoxy group of 1 to 4 carbon atoms, with the proviso that when m represents an integer of two or more, plural $R^8$s may be different each, and $R^9$ represents a hydrogen atom, an alkyl group of 1 to 4 carbon atoms or a phenyl group, with the proviso that two of $R^9$ may be different each)), $R^3$ represents a hydrogen atom, a halogen atom, an alkyl group of 1 to 4 carbon atoms or two of $R^3$ and a phenyl group to which two of $R^3$ are linked, together represent a naphthyl group of the general formula:

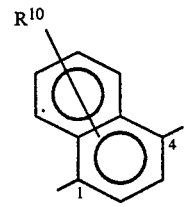

(wherein $R^{10}$ represents a hydrogen atom, a halogen atom or an alkyl group of 1 to 4 carbon atoms), with the proviso that when $R^1$ represents a hydrogen atom, the hydrogen atom may be replaced by $R^3$, and n represents an integer of 1 to 3, with the proviso that when n represents an integer of two or more, plural $R^3$s may be different each, X represents an oxygen atom or a sulfur atom and $R^4$ represents an amino acid-residue].

This step is reaction of forming amide-bond. The reaction to form amide-bond from an acid and an amine is well known, for example, (A) by the method with using mixed acid anhydride (B) by the method with using acid halide (C) by the method with using DCC etc.

Concrete description of these methods described above are as follows:

(A) method with using mixed acid anhydride may be carried out, for example, by reacting an acid of the general formula (II) with an acid halide (pivaloyl chloride, thionyl chloride, tosyl chloride, mesyl chloride, oxalyl chloride etc.) or an acid derivative (ethyl chloroformate, isobutyl chloroformate etc.) in an inert organic solvent (chloroform, methylene chloride, diethyl ether, THF etc.) or without solvents in the presence of tertiary amine (pyridine, triethylamine, picoline etc.), at from 0° C. to 40° C. to give a mixed acid anhydride. The obtained acid mixed anhydride and an amine of the general formula (III) are reacted in an inert organic solvent (described above), at from 0° C. to 40° C.

(B) method with using acid halide may be carried out, for example, by reacting an acid of the general formula (II) with acid halide (described above) in an inert organic solvent (described above) or without solvents at from −20° C. to a refluxing temperature to give an acid halide. The obtained acid halide and an amine of the general formula (III) are reacted in an inert organic solvent (described above) in the presence or absence of tertiary amine (described above) at from −5° C. to 40° C.

(C) method with using DCC may be carried out, for example, by reacting an acid of the general formula (II) and an amine of the general formula (III) in an inert organic solvent (described above) or without solvents in the presence or absence of tertiary amine (described above) using with DCC (dicyclohexylcarbodiimide) at from 0° C. to 40° C.

Preferably, the reactions (A), (B) and (C) described above are carried out in an atmosphere of an inert gas (argon, nitrogen etc.) on anhydrous condition. Hereupon the method (B) with using acid halide is preferred.

In the compounds of the general formula (II) used as a starting material, when $R^1$ represents a hydrogen atom and $R^2$ represents the group of the general formula —$COR^7$ (wherein $R^7$ is the same meaning as described hereinbefore), that is, the compound of the general formula:

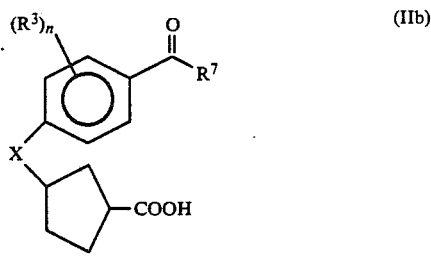

(IIb)

[wherein all symbols are the same meaning as described hereinbefore] can be prepared by the method described in the specifications of European patent application No. 86305327.8 (filed on July 11th, 1986) and U.S. patent application Ser. No. 06/887,772 (filed on July 21st, 1986).

And in the compounds of the general formula (II), when $R^1$, $R^2$ and a phenyl group to which $R^1$ and $R^2$ are linked, together represent an indanyloxy group, that is, the compunds of the general formula:

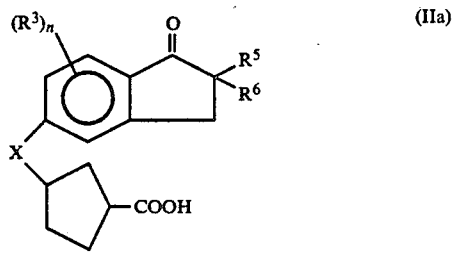

(IIa)

[wherein all symbols are the same meaning as described hereinbefore] can be prepared by the following scheme.

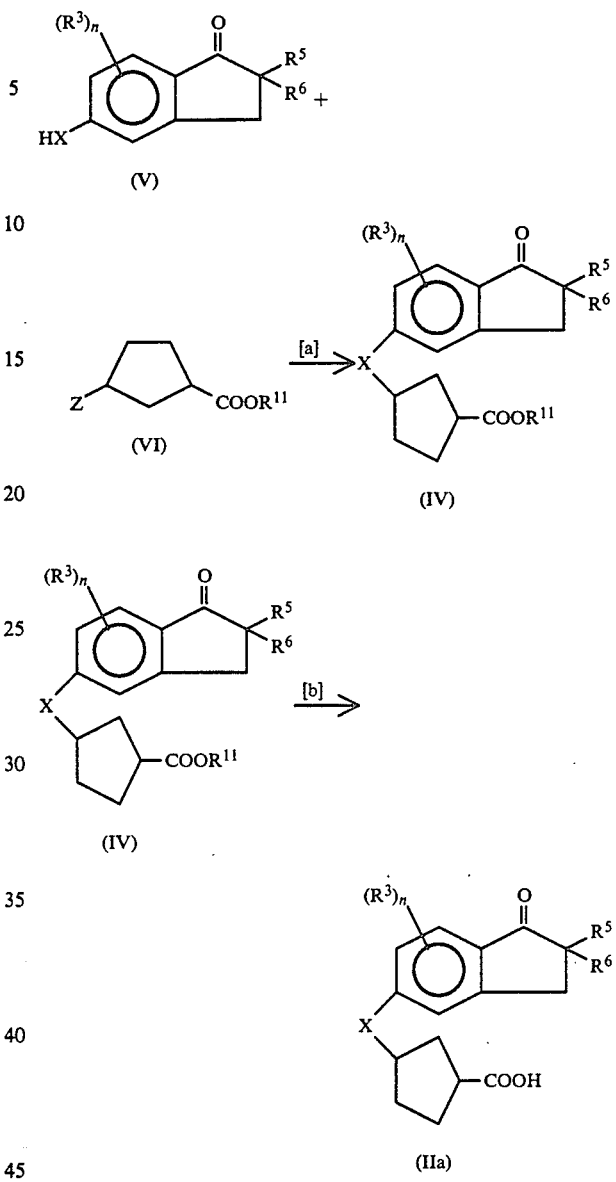

[wherein Z represents a halogen atom (e.g. chlorine, bromine, iodine atom) or a substituted or unsubstituted alkylsulfonyloxy or arylsulfonyloxy group (e.g. methanesulfonyloxy group, p-toluenesulfonyloxy group), $R^{11}$ represents an alkyl group of 1 to 4 carbon atoms, the other symbols are the same meaning as described hereinbefore].

The step [a] may be carried out by the method described in the specifications of European Patent Publication No. 181100 and U.S. patent application Ser. No. 06/792,399 (filed on Oct. 29th, 1985). Hereupon the compound of the general formula (V) using as starting material can be prepared by the method described in Derwent Publications Ltd. World Patent Index Acc. No. 74-32654V/18 and Derwent Publications Ltd. World Patent Index Acc. No. 82-20160E/11, and the compound of the general formula (VI) can be prepared by the method described in the specifications of European Patent Publication No. 181100 and U.S. patent application Ser. No. 06/792,399 (filed on Oct. 29th, 1985).

And the step [b] is a saponification reaction and may be carried out by the reaction in the presence of a solvent soluble in water, for example tetrahydrofurane or an alkanol of 1 to 4 carbon atoms (e.g. methanol), using an aqueous solution of a hydroxide or carbonate of an alkali metal, for example, lithium, sodium or potassium, at a temperature from 0° C. to an ambient temperature.

As the compound of the general formula (III), another starting material, a reagent which is on the market can be used.

The compound of the general formula (I), prepared by the above methods, can be purified by the conventional methods for purification, for example, by the methods of column chromatography on silica gel, washing with water or recrystallization.

And the compounds of the general formula (I) may be converted into salts by known methods.

The salts are preferably non-toxic and water-soluble. Suitable salts are, for example, a salt of such an alkali metal as sodium or potassium, a salt of such an alkaline earth metal as calcium or magnesium, or an ammonium salt or a non-toxic amine salt, for example, such a tetraalkylammonium salt as tetramethylammonium salt or such an organic amine salt as methylamine, dimethylamine, cyclopentylamine, benzylamine, phenetylamine, piperidine, monoethanolamine, diethanolamine, tris(hydroxymethyl)aminomethane, lysine, arginine or N-methyl-D-glucamine salts.

EFFECT

The compounds of the general formula (I) and their nontoxic salts have a potent inhibitory effect on development of cerebral edema.

A group of diseases which cause cerebral edema is such diseases of cerebral ischemia as cerebral blood vascular damage (e.g. cerebral infarction, cerebral thrombosis), decrease of cerebral blood flow, cerebral ischemia, cerebral anoxia or spinal cord damage. In these diseases, because of the deficiency in oxygen supplied to organs, the level of energy production decreases, and then it becomes impossible to maintain the exchange reaction of $Na^+ \longleftrightarrow K^+$ across the cell membranes by ATPase (adenosinetriphosphatase), and further the intracellular concentration of $Na^+$ and $Cl^-$ increases. Accordingly, because extracellular water is taken into the cell, cerebral edema is developed. Another group of diseases which cause cerebral edema is such diseases that bring about the physical compression as cephalic trauma or cerebral tumor. In these diseases, it has been also considered that a damage in cellular function by physical compression leads $Na^+$ influx followed by water influx into the cells, and then edema is developed.

The compounds of the general formula (I) and their nontoxic salts inhibit the influx of $Na^+$ and $Cl^-$, and of water into cells and therefore potently inhibit the formation of cerebral edema. Accordingly, they are useful for the prevention of and the treatment of cerebral edema caused by any diseases as mentioned above.

The inhibitory effect on cerebral edema of the compounds of the present invention, was confirmed by pharmacological experiments in vitro and in vivo, for example, by the following screening test.

THE INHIBITION TEST ON CEREBRAL EDEMA USING ORGAN SLICE OF CAT CEREBRAL CORTEX

The test was carried out by the method described in Journal of Medicinal Chemistry, Vol. 25 (No. 5), 567 (1982).

That is, brain was isolated from a cat (weighing 2~4 kg), slices of about 1 mm in thickness was prepared, the white matter substance was removed, and the gray matter substance (100~150 mg a test) was used for a sample. The sample was added to the following incubation medium and incubated for 50 minutes at 37° C. After the incubation, the sample was immediately weighed again to determine the swelling weight of the sample.

| incubation medium (osmotic pressure, 280~290 mOsm/l) | |
|---|---|
| 1. Hepes Buffer (pH 7.4) . . . 2.365 ml | |
| glucose | 10 mM |
| CaCl$_2$ | 1.3 mM |
| MgSO$_4$ | 1.2 mM |
| KH$_2$PO$_4$ | 1.2 mM |
| Hepes | 20 mM |
| NaCl | 122 mM |
| KCl | 20 mM |
| adjusted to pH 7.4 by NaOH | |
| 2. test compounds dissolved in the presence of tris-(hydroxymethyl)aminomethanel or water . . . 0.01 ml | |
| 3. 0.2 M NaHCO$_3$ . . . 0.125 ml (dissolved by Hepes Buffer, giving the final concentration of 10 mM in medium) | |

The test was carried out by using NaHCO$_3$ as a stimulating agent of swelling.

(A) A percentage of swelling when a slice sample was added to incubation medium comprising Hepes Buffer, water and NaHCO$_3$ (defined as maximum of swelling).

(B) A percentage of swelling when a slice sample was added to incubation medium comprising Hepes Buffer and water (defined as maximum inhibition of swelling).

(C) A percentage of swelling when a slice sample was added to incubation medium comprising Hepes Buffer, the test compounds in various concentrations and NaHCO$_3$.

Above-mentioned (A), (B) and (C) were determined. Inhibition percentage of the test compounds was calculated by the following equation:

$$\text{inhibition \%} = \frac{(A) - (C)}{(A) - (B)} \times 100$$

IC$_{50}$ value was determined by dose-response curve as a concentration in which inhibition percentage was 50.

The results are shown in Table I.

TABLE I

| Inhibitory effect on cerebral edema | |
|---|---|
| Example No. of test compound | Inhibitory activity on cerebral edema (IC$_{50}$, M) |
| 1 | $3.0 \times 10^{-6}$ |
| 1-(c) | $5.0 \times 10^{-7}$ |
| 1-(j) | $3.4 \times 10^{-6}$ |
| 1-(m) | $5.7 \times 10^{-6}$ |

From the above result, every parent compounds of the general formula (II) to which an amino acid of the general formula (III) is bonded, can be confirmed to have an inhibitory activity on cerebral edema. Accordingly, it can be expected that all the compounds of the present invention of the general formula (I) have an inhibitory activity on cerebral edema.

And the toxicity of compounds of the present invention are enough low, and therefore, they can be confirmed to be able to use enough safety as drug.

For example, in the acute toxicity test in mice by intravenous administration, $LD_{50}$ value of compounds of example 1 and 1-(c) is the dose of between 200 and 400 mg/kg.

Accordingly the compounds of the present invention are useful for prevention and treatment for cerebral edema in mammal, specifically human being in those.

For the purpose of the prevention and the treatment for cerebral edema, the compounds of the general formula (I) or nontoxic salts thereof may normally be administered systemically or partially, usually by oral or parenteral administration. The dose to be administered is determined depending upon age, body weight, symptom, the desired therapeutic effect, the route of administration, and the duration of the treatment etc. In the human adult, the doses per person for one time are generally between 1 mg and 1 g, by oral administration up to several times per day, and between 100 $\mu$g and 100 mg, by parenteral administration (preferably by intravenous administration) up to several times per day.

As mentioned above, the doses to be used depend on various conditions. Therefore, there are cases in which doses lower than the ranges specified above and doses greater than the ranges specified above, may be used.

Solid compositions according to the present invention for oral administration include compressed tablets, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium gluconate, stabilizing agents such as lactose, and solubilizers such as glutamic acid and asparaginic acid. The tablets or pills may, if desired, be made into gastric film-coated or enteric film-coated tablets or pills, such as sugar-coated, gelatin-coated, hydroxypropylcellulose-coated or hydroxypropylmethylcellulose phthalate-coated tablets or pills; two or more layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, Polysorbate 80 (registered Trade Mark). These compositions may also include adjuvants such as preserving agents, wetting agents, emulsifying agents, dispersing agents, stabilizing agents (e.g. lactose) and solubilizers (e.g. glutamic acid and asparaginic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

EXAMPLES

The following Examples illustrate the preparation of compounds of the present invention, however, the present invention is not restricted to them. In the Examples, "TLC", "NMR", "IR" and "MS" represent "Thin layer chromatography", "Nuclear magnetic resonance spectrum", "Infrared absorption spectrum" and "Mass spectrum", respectively. The solvents in parenthesis specified in chromatographic separations show the developing solvents or the elution solvent, and the ratios of the solvent are shown by volume. Except when specified otherwise, infrared absorption spectra were recorded by KBr tablet and nuclear magnetic resonance spectra were recorded in deuterochloroform ($CDCl_3$) solution.

EXAMPLE 1

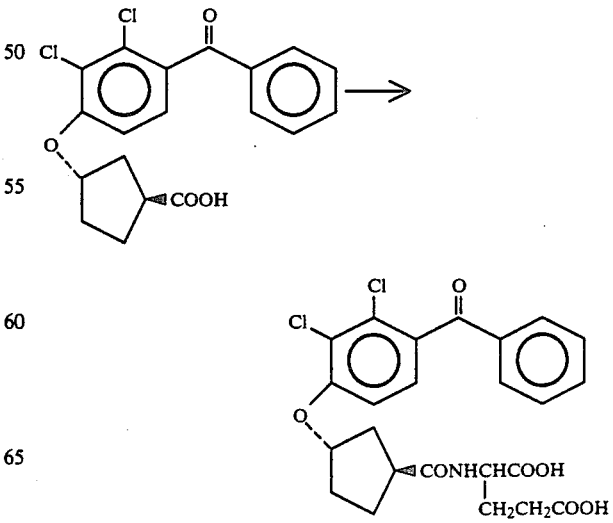

Process 758 mg of (1S,3S)-3-(2,3-dichloro-4-benzoylphenoxy)cyclopentane carboxylic acid (prepared by the method described in Example 1 in the specification of European patent application No. 86305327.8 and U.S. patent application Ser. No. 06/887,772 (filed on July 21st, 1986) was dissolved in 2 ml of methylene chloride, and further 1.269 g of oxalyl chloride was added thereto. The mixture was stirred for 2 hours at ambient temperature and concentrated under reduced pressure.

882 mg of L-glutamic acid was dissolved in 3 ml of a 4N aqueous solution of sodium hydroxide and cooled on ice. 1 ml of tetrahydrofuran was added into the mixture and the acid chloride obtained by above-mentioned method was added slowly dropwise to the mixture with violently stirring under cooling with ice.

The reaction mixture was stirred for 30 minutes under cooling with ice and then stirred for 1 hour at ambient temperature. The mixture was acidified by adding a diluted hydrochloric acid and was extracted with 15 ml of ethyl acetate. The extract was washed with a saturated aqueous solution of sodium chloride, dried over anhydrous magnesium sulfate, and concentrated under reduced pressure to give 990 mg of crude product.

Purification

[A] Method by using column chromatography

| | |
|---|---|
| obtained crude product | 14.1 g |
| silica gel | 260 g |
| elution solvent | |
| first . . . methylene chloride: ethanol = 20:1 | |
| after eluting the starting material | |
| . . . methylene chloride: ethanol = 8:1 | |
| -continued | |
| obtained title compound | 9.741 g |

[B] Method by using dicyclohexylamine 990 mg of crude product obtained by the above-mentioned process was dissolved in 10 ml of acetonitrile, and 760 mg of dicyclohexylamine was added dropwise to the mixture with stirring. The reaction mixture was refluxed for 20 minutes, and then allowed to stand overnight. The precipitated crystal was filtered off to give 1.578 g of the dicyclohexylamine salt. The obtained dicyclohexylamine salt was dissolved in an aqueous solution of sodium bisulfate, and extracted with ethyl acetate. The extract was washed with water, dried over anhydrous sodium sulfate and concentrated under reduced pressure to give 920 mg of the title compound.

Melting point: 68°~74° C.;

TLC (chloroform:methanol:acetic acid=200:20:5): Rf 0.12;

NMR: $\delta$ 7.76 (2H,d), 7.57 (1H,t), 7.42 (2H,t), 7.24 (1H,d), 6.90 (1H,d), 6.7~6.85 (1H,m), 5.0 (1H,m), 4.5~4.7 (1H,m), 2.95~3.2 (1H,m), 1.8~2.6 (10H,m);

IR: $\nu$ 3300, 2950, 1720, 1660, 1580, 1540, 1450, 1390, 1280, 1000;

MS: m/z 489, 453, 445, 378, 266.

Hereafter, the various compounds were obtained by the same procedure as described in Example 1. As the starting materials, an amino acid used was one on the market and a carboxylic acid was prepared by the method described in Derwent Publications Ltd. World Patent Index Acc. No. 82-20160 E/11, and in the specifications of European Patent Publication No. 181100, U.S. patent application Ser. No. 06/792,399 (filed on Oct. 29th, 1985), European Patent Application No. 86305327,8 (filed on July 11th, 1986) and U.S. patent application Ser. No. 06/887,772 (filed on July 21st, 1986).

The results are shown in Table II.

TABLE II $$\underset{(R^3)_n}{\overset{R^1}{\bigodot}}\underset{X}{\overset{R^2}{\bigodot}}\overset{CONH-R^4}{\bigodot} \quad (I)$$

| Example No. | $\underset{(R^3)_n}{\overset{R^1}{\bigodot}}\overset{R^2}{X}$ | —NH—R⁴ | TLC: value of Rf (developing solvent) | IR: ν | Purification(*) |
|---|---|---|---|---|---|
| 1-(a) | 2,3-dichloro-4-hydroxybenzoyl-phenyl | —NHCH₂COOH | 0.30 (acetic acid:methanol: methylenechloride = 1:1:10) | 3400, 2830, 1740, 1670, 1580, 1460, 1320, 1280, 1220, 1010 cm⁻¹ | column chromatography |
| 1-(b) | 2,3-dichloro-4-hydroxybenzoyl-phenyl | —NH(CH₂)₃COOH | 0.45 (acetic acid:methanol: chloroform = 1:1:10) | 2950, 1700, 1670, 1580, 1460, 1445, 1380, 1315, 1270, 1165, 1000, 970, 820, 740, 710 cm⁻¹ | column chromatography |
| 1-(c) | 2,3-dichloro-4-hydroxybenzoyl-phenyl | —NHCHCOOH<br>  \|<br>  CH₃ | 0.53 (chloroform:methanol: acetic acid = 200:20:5) | 3300~2500, 1760, 1640, 1580, 1540, 1450 cm⁻¹ | recrystallization |
| 1-(d) | 2,3-dichloro-4-hydroxybenzoyl-phenyl | —NH(CH₂)₂COOH | 0.22 (chloroform:methanol = 10:1) | 3300~2700, 1710, 1670, 1650, 1590, 1550, 1470, 1450 cm⁻¹ | column chromatography |

TABLE II-continued (structure: (R³)ₙ-phenyl-X-cyclopentyl with R¹, R² on phenyl and CONH-R⁴ on cyclopentane) (I)

| Example No. | (parent structure with R¹, R², (R³)ₙ, X) | —NH—R⁴ | TLC: value of Rf (developing solvent) | IR: ν | Purification(*) |
|---|---|---|---|---|---|
| 1-(e) | 2,3-dichloro-4-hydroxyphenyl benzoyl | —NHCHCOOH<br>\|<br>CH₂OH | 0.21 (chloroform:methanol: acetic acid = 200:20:5) | 3400~2500, 1740, 1650, 1580, 1540 cm⁻¹ | recrystallization |
| 1-(f) | 2,3-dichloro-4-hydroxyphenyl benzoyl | —NHCHCOOH<br>\|<br>CH₂COOH | 0.14 (chloroform:methanol: acetic acid = 200:20:5) | 3400~2500, 1740, 1720, 1660, 1620, 1580, 1520, 1460, 1440 cm⁻¹ | recrystallization |
| 1-(g) | 2,3-dichloro-4-hydroxyphenyl benzoyl | —NHCHCOOH<br>\|<br>CH₂CONH₂ | 0.10 (chloroform:methanol: acetic acid = 200:20:5) | 3400~2500, 1720, 1660, 1580, 1460 cm⁻¹ | washing with hot ethyl acetate |
| 1-(h) | 2,3-dichloro-4-hydroxyphenyl benzoyl | —NHCH₂CHCH₂COOH<br>\|<br>OH | 0.31 (chloroform:methanol: acetic acid = 200:20:5) | 3400~2500, 1720, 1660, 1630, 1580, 1530, 1460 cm⁻¹ | recrystallization |

TABLE II-continued $$\underset{(R^3)_n}{\underset{X}{\bigodot}}\underset{R^2}{\overset{R^1}{\bigodot}}-CONH-R^4 \quad (I)$$

| Example No. | 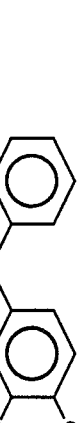 structure | —NH—R⁴ | TLC: value of Rf (developing solvent) | IR: ν | Purification(*) |
|---|---|---|---|---|---|
| 1-(i) | 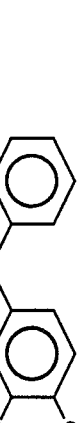 | —NHCHCOOH<br>    |<br>CH₂CH₂CONH₂ | 0.16<br>(chloroform:methanol:<br>acetic acid = 200:20:5) | 3500~2300, 1720, 1660,<br>1580, 1450, 1280,<br>1000 cm⁻¹ | column chromatography |
| 1-(j) |  | —NHCHCOOH<br>    |<br>CH₂CH₂COOH | 0.3<br>(methanol:<br>methylenechloride = 1:5) | 3300, 2950, 1700, 1570,<br>1440, 1400, 1290, 1265,<br>1160, 1140, 1040,<br>750 cm⁻¹ | column chromatography |
| 1-(k) |  | —NHCHCOOH<br>    |<br>CH₂CH₂COOH | 0.1<br>(methanol:<br>methylenechloride = 1:5) | 3350, 2940, 1720, 1650,<br>1605, 1580, 1445, 1380,<br>1270, 1000, 760 cm⁻¹ | column chromatography |
| 1-(l) | 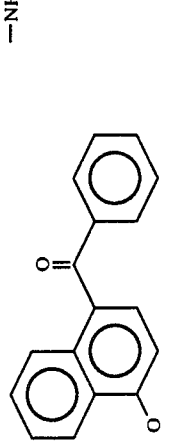 | —NHCHCOOH<br>    |<br>CH₂CH₂COOH | 0.10<br>(methanol:<br>methylenechloride = 1:5) | 3300, 2925, 1720, 1630,<br>1570, 1420, 1330, 1250,<br>1170, 1080, 1050, 1020,<br>770, 710 cm⁻¹ | column chromatography |

TABLE II-continued $$(R^3)_n \underset{X}{\overset{R^1}{\underset{R^2}{\bigcirc}}} \quad (R^3)_n \underset{}{\overset{R^1}{\underset{R^2}{\bigcirc}}} \underset{}{\overset{}{\bigcirc}} CONH-R^4 \quad (I)$$

| Example No. | (structure) | —NH—R⁴ | TLC: value of Rf (developing solvent) | IR: ν | Purification(*) |
|---|---|---|---|---|---|
| 1-(m) | 2,3-dichloro-4-hydroxyphenyl 2-thienyl ketone | —NHCHCOOH<br>    \|<br>CH₂CH₂COOH | 0.10<br>(methanol:<br>methylenechloride = 1:5) | 3370, 2920, 1710, 1640, 1580, 1460, 1410, 1270, 1000, 730 cm⁻¹ | column chromatography |
| 1-(n) | (2,3-dichloro-4-hydroxyphenyl)(1-naphthyl) ketone | —NHCHCOOH<br>    \|<br>CH₂CH₂COOH | 0.10<br>(methanol:<br>methylenechloride = 1:5) | 3400, 2920, 1710, 1640, 1575, 1450, 1380, 1270, 1245, 1000, 780 cm⁻¹ | column chromatography |
| 1-(o) | 1-(2,3-dichloro-4-hydroxyphenyl)-2-phenyl ethanone | —NHCHCOOH<br>    \|<br>CH₂CH₂COOH | 0.10<br>(methanol:<br>methylenechloride = 1:5) | 3370, 2940, 1720, 1660, 1575, 1540, 1460, 1390, 1280, 1220, 1170, 1120, 1000, 760, 720, 680, 660 cm⁻¹ | column chromatography |

(*) In purification, as the elution solvent of column chromatography, the same solvent used in Example 1 was used, and as the solvent for recrystallization, ethyl acetate-hexane system was used.

In the compounds of Example 1 to 1(o) mentioned above, the stereo-configuration of the carbon atoms at the 1- and 3-positions of the cyclopentylene group is (1S,3S).

The compounds having the stereo-configuration except for (1S,3S), were prepared by using as the starting material the compound described in the specification of European Patent Publication No. 181100.

The results are shown in Table III.

TABLE III

[structure: 2,3-dichloro-4-benzoyl-phenoxy cyclopentane CONHCHCOOH with CH₂CH₂COOH side chain]

| Example No. | Configuration | TLC: value of Rf (elusion solvent) | IR: $\nu$ | Method of purify |
|---|---|---|---|---|
| 1-(p) | (1R,3R) | 0.10 (methanol: methylenechloride = 1:5) | 3300, 2900, 1700, 1630, 1560, 1610, 1370, 1250, 1150, 980, 690 cm$^{-1}$ | column chromatography |
| 1-(q) | (1R,3S) | 0.10 (methanol: methylenechloride = 1:5) | 3400, 2950, 1720, 1660, 1585, 1540, 1470, 1450, 1390, 1320, 1275, 1000, 800, 770, 740, 710, 660 cm$^{-1}$ | column chromatography |

EXAMPLE 2

500 mg of N-{(1S,3S)-3-(2,3-dichloro-4-benzoyl-phenoxy)cyclopentanecarbonyl}glutamic acid (prepared in Example 1) was dissolved in 5 ml of ethanol and the solution was sterilized by filtration through a bacteria-retaining filter, and placed 0.1 ml portions into 1 ml ampoules to obtain ampoules each containing 10 mg of the active ingredient, and the ampoules were then sealed. The contents of ampoules are used for injection by diluting with a suitable quantity of diluent, for example, by diluting with a trishydrochloric acid buffer solution (pH 8.6) to 1 ml.

What is claimed is:

1. A derivative of 3-phenoxy or phenylthio cyclopentanecarbonylamino acid of the formula:

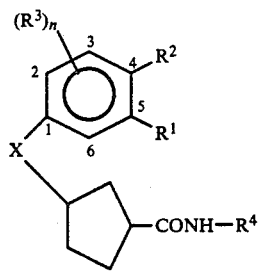

(I)

$R^1$ represents a hydrogen atom and $R^2$ represents the group of the formula: —$COR^7$ wherein $R^7$ represents the group of the formula:

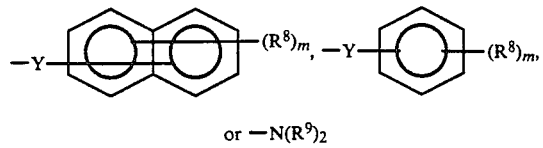

or —$N(R^9)_2$ wherein Y represents a single-bond, an alkylene group or an alkenylene group of 1 to 4 carbon atoms, m represents an integer of 1 to 3, $R^8$ represents a hydrogen atom, a halogen atom, a nitro group, a hydroxy group or an alkyl group or an alkoxy group of 1 to 4 carbon atoms, with the proviso that when m represents an integer of two or more, plural $R^8$s may be different each, and $R^9$ represents a hydrogen atom, an alkyl group of 1 to 4 carbon atoms or a phenyl group, with the proviso that two of $R^9$ may be different each, $R^3$ represents a hydrogen atom, a halogen atom, an alkyl group of 1 to 4 carbon atoms or two of $R^3$ and a phenyl group to which two of $R^3$ are linked, together represent a naphthyl group of the formula:

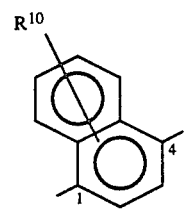

wherein $R^{10}$ represents a hydrogen atom, a halogen atom or an alkyl group of 1 to 4 carbon atoms, with the proviso that when $R^1$ represents a hydrogen atom, the hydrogen atom may be replaced by $R^3$, and n represents an integer of 1 to 3, with the proviso that when n represents an integer of two or more, plural $R^3$s may be different, X represents an oxygen atom or a sulfur atom and $R^4$ represents an amino acid radical selected from the group consisting of alanine, β-alanine, asparagine, 4-aminobutyric acid, glycine, glutamine, serine, phenylalanine, cysteine, 4-amino-3-hydroxybutyric acid, tryptophane, leucine, isoleucine, threonine, methionine, proline, valine, glutamic acid, asparaginic acid, lysine, arginine and histidine, or a non-toxic salt thereof.

2. A derivative according to claim 1 in which $R^4$ is a glutamic acid or asparaginic acid radical.

3. A derivative according to claim 1 in which $R^4$ is a neutral amino acid radical selected from the group consisting of alanine, β-alanine, asparagine, 4-aminobutyric acid, glycine, glutamine, serine, phenylalanine, cysteine, 4-amino-3-hydroxybutyric acid, tryptophane, leucine, isoleucine, threonine, methionine, proline and valine.

4. A derivative according to claim 1, which is

N-{(1S,3S)-3-(2,3-dichloro-4-benzoylphenoxy)cyclopentanecarbonyl}glycine,

4-{(1S,3S)-3-(2,3-dichloro-4-benzoylphenoxy)cyclopentanecarboxamido}butyric acid, N-{(1S,3S)-3-(2,3-dichloro-4-benzoylphenoxy)cyclopentanecarbonyl}alanine, N-{(1S,3S)-3-(2,3-dichloro-4-benzoylphenoxy)cyclopentanecarbonyl}-β-alanine, N-{(1S,3S)-3-(2,3-dichloro-4-benzoylphenoxy)cyclopentanecarbonyl}serine, N-{(1S,3S)-3-(2,3-dichloro-4-benzoylphenoxy)cyclopentanecarbonyl}asparaginic acid, N-{(1S,3S)-3-(2,3-dichloro-4-benzoylphenoxy)cyclopentanecarbonyl}asparagine, 4-{(1S,3S)-3-(2,3-dichloro-4-benzoylphenoxy)cyclopentanecarboxamido}-3-hydroxy butyric acid, N-{(1S,3S)-3-(2,3-dichloro-4-benzoylphenoxy)cyclopentanecarbonyl}glutamic acid, N-{(1S,3S)-3-(2,3-dichloro-4-benzoylphenylthio)cyclopentanecarbonyl}glutamic acid, N-{(1S,3S)-3-(2,3-dichloro-4-benzoylphenoxy)cyclopentanecarbonyl}glutamine, N-[(1S,3S)-3-{2,3-dichloro-4-(2-fluorobenzoyl)phenoxy}cyclopentanecarbonyl]glutamic acid, N-{(1S,3S)-3-(4-benzoyl-1-naphthoxy)cyclopentanecarbonyl}glutamic acid, N-[(1S,3S)-3-{2,3-dichloro-4-(1-naphthoyl)phenoxy}cyclopentanecarbonyl]glutamic acid, N-{(1S,3S)-3-(2,3-dichloro-4-phenylacetylphenoxy)cyclopentanecarbonyl}glutamic acid, N-{(1R,3R)-3-(2,3-dichloro-4-benzoylphenoxy)cyclopentanecarbonyl}glutamic acid, or N-{(1R,3S)-3-(2,3-dichloro-4-benzoylphenoxy)cyclopentanecarbonyl}glutamic acid.

5. A pharmaceutical composition for the treatment of cerebral edema characterized by comprising as an active ingredient, an effective amount of a compound of the formula (I) described in claim 1, wherein various symbols are as defined in claim 1, or a non-toxic salt thereof together with a pharmaceutically acceptable carrier.

6. A method for the treatment of cerebral edema, which comprises the administration of an effective amount of a compound of the formula (I) described in claim 1, wherein various symbols are as defined in claim 1, or a non-toxic salt thereof to a patient in need of treatment of cerebral edema.

* * * * *